United States Patent [19]

Mason

[11] Patent Number: 4,676,750

[45] Date of Patent: Jun. 30, 1987

[54] DENTAL DRILL SYSTEM

[76] Inventor: Michael S. Mason, 8190 SW. Nimbus, Beaverton, Oreg. 97005

[21] Appl. No.: 695,167

[22] Filed: Jan. 25, 1985

[51] Int. Cl.⁴ ............................................... A61C 1/02
[52] U.S. Cl. ..................................... 433/101; 433/28; 433/98
[58] Field of Search ...................... 433/28, 101, 98, 99

[56] References Cited

U.S. PATENT DOCUMENTS

| | | | |
|---|---|---|---|
| 3,476,153 | 11/1969 | Roland | 433/101 |
| 3,556,669 | 1/1971 | Valeska et al. | 433/101 |
| 3,638,310 | 2/1972 | Austin, Jr. | 433/28 |
| 3,855,704 | 12/1974 | Booth | 433/101 |
| 3,918,161 | 11/1975 | Morgan et al. | 433/28 |
| 4,118,866 | 10/1978 | Ross et al. | 433/101 |
| 4,136,450 | 1/1979 | Guenther et al. | 433/98 |
| 4,201,051 | 5/1980 | Hall | 433/101 |
| 4,230,143 | 10/1980 | Dettmann et al. | 433/98 |

FOREIGN PATENT DOCUMENTS 1446033  8/1976  United Kingdom ................. 433/98

Primary Examiner—John J. Wilson
Attorney, Agent, or Firm—Robert L. Harrington

[57] ABSTRACT

A dental drill system including a multiple of drills operated through a modular control setup by a single foot control unit. The moduler control setup includes an individual module for each hand drill, a syringe block, and a manifold to which the foot control unit is connected. The foot control unit produces the controlling functions by pressurizing different ones of a plurality of air lines connected into the manifold. Multiple orifices extended through the modules and into the manifold provides common air pressure from the foot control lines to each of the modules, and is referred to as a primary orifice network. A secondary orifice network in each module taps into the primary orifice and converts the foot control line pressures into the various dental drill functions i.e. drilling with cooling air, drilling with mist air and chip air. A valve structure in each module is activated by a dental drill holding arm to open and close the interconnection between the first and second orifice networks in response to removal and placement of the dental drill in the holder.

16 Claims, 16 Drawing Figures

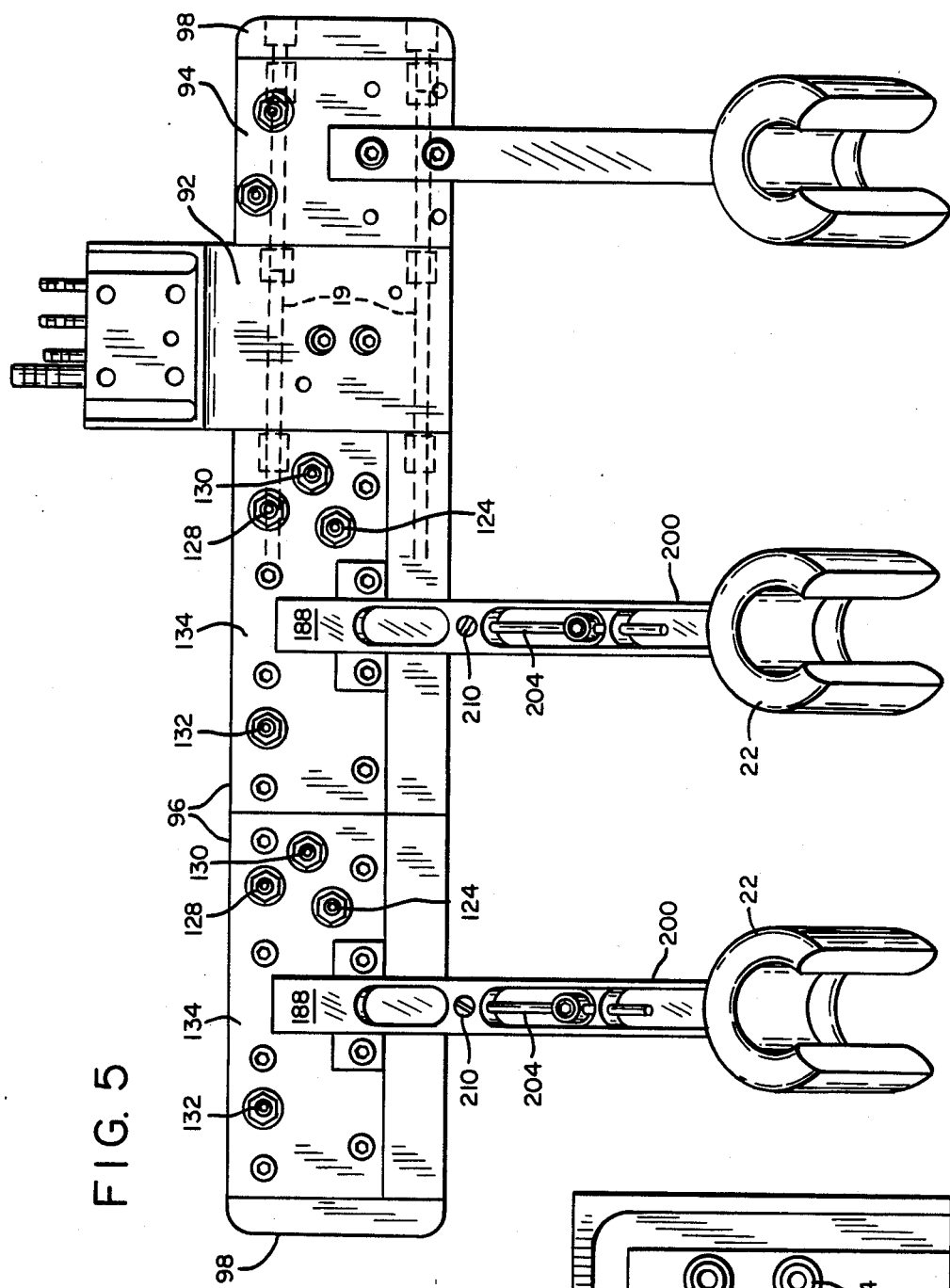
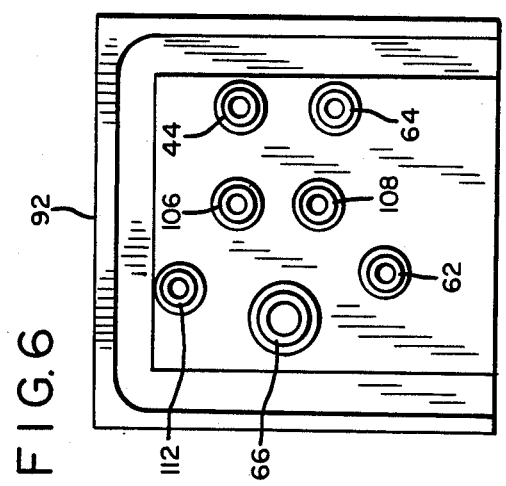
FIG. 5
FIG. 6

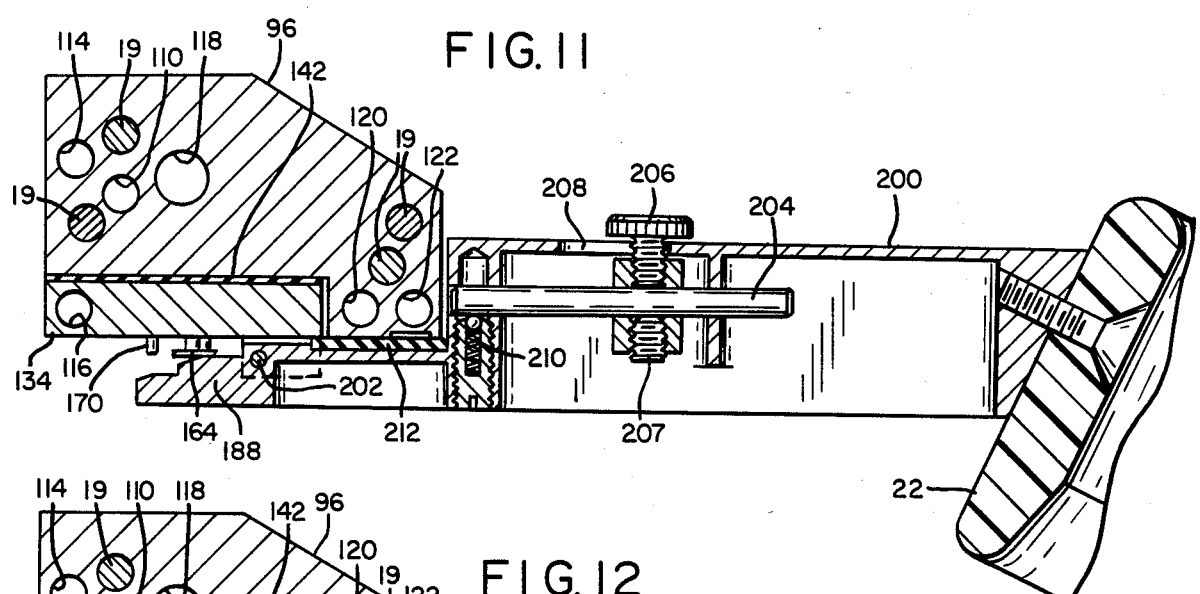
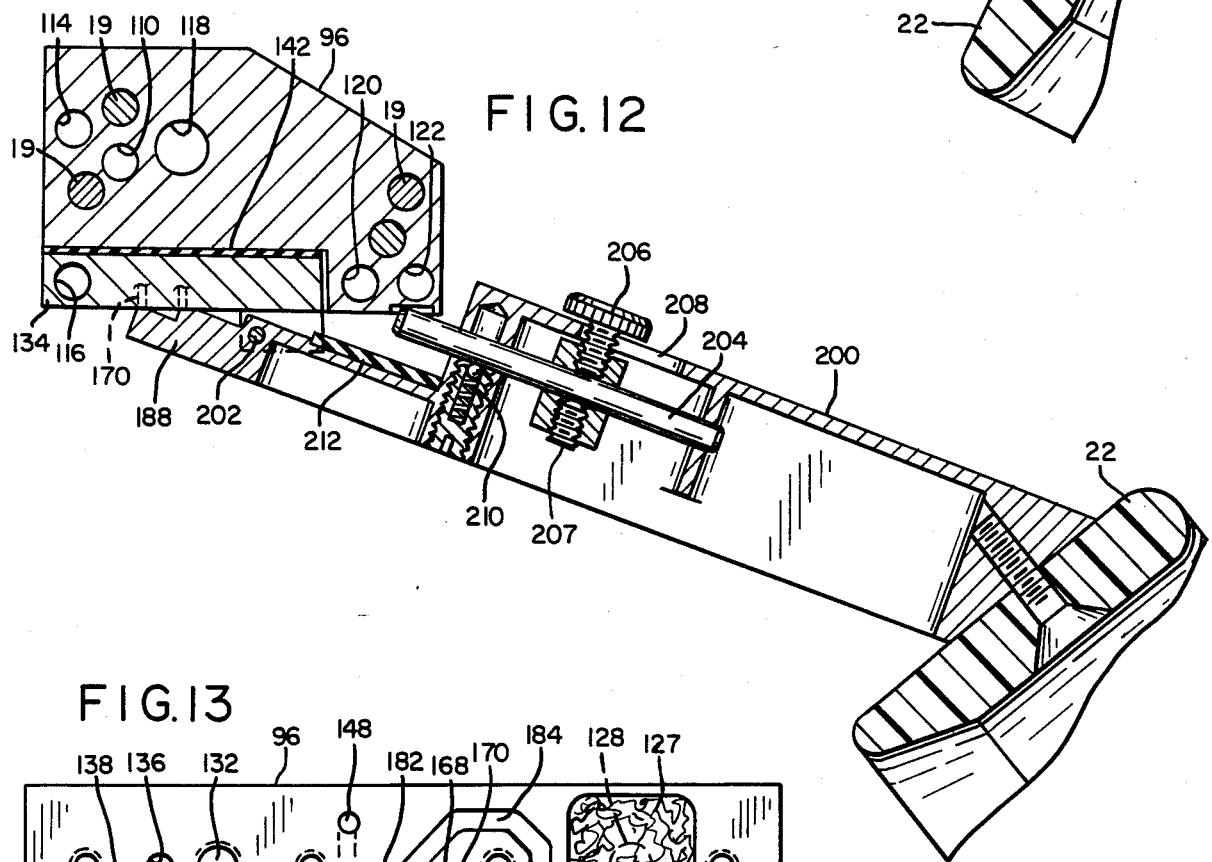
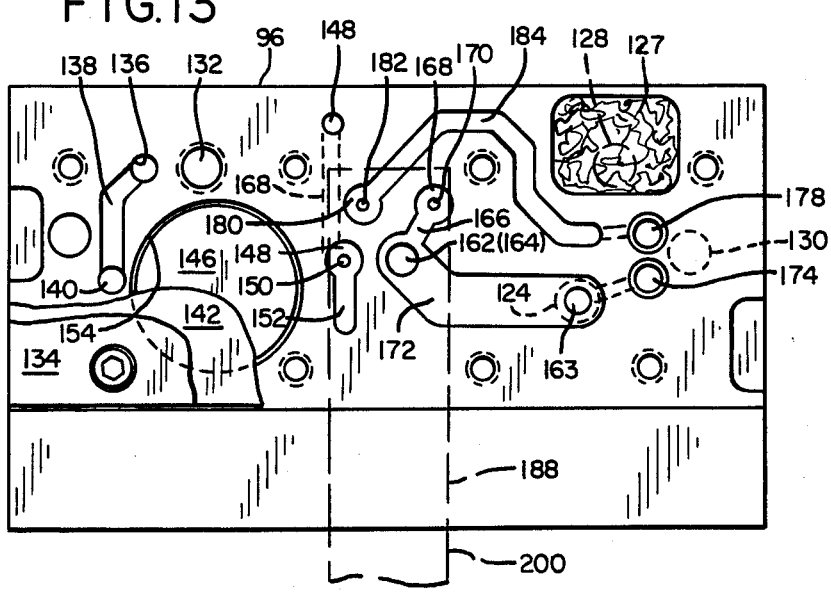

DENTAL DRILL SYSTEM

FIELD OF INVENTION

This invention relates to a system and components thereof for supplying air and water to multiple hand drills used by dentists for drilling teeth.

HISTORY OF INVENTION

A dental hand drill designed to be driven by air as contemplated by the present invention encompasses a hand piece having an internal air tight chamber connected to air inlet and outlet lines. A turbine in the chamber is rotated by circulation of the air through the chamber. A drill bit having its shaft inserted through the hand piece housing is coupled to the turbine and driven by rotation of the turbine.

The protruding head of the drill bit is used to grind a dental patient's teeth, and during the grinding operation becomes hot. Thus the hand piece housing typically includes a nozzle that is connected to an air supply line that directs cooling air against the grinding head of the drill bit. On occasion, as determined by the dentist, it is desirable to cool the grinding head of the bit with mist and thus the nozzle is also coupled to a water supply line. As a further function during the drilling operation, it is often desirable to clean the area around the tooth being worked on with air only from the nozzle (the drill bit being passive). Thus the controlled functions of the drill bit as contemplated for the hand drill of this invention includes (a) drilling coupled with cooling air, (b) drilling coupled with cooling mist and (c) air only from the nozzle for cleaning around the tooth area, hereafter referred to as chip air.

Because it is important for the dentist to carefully control the movements of the hand drill during the drilling operation and because it is necessary to turn the multiple functions on and off during the drilling operation, the on/off controls are foot controlled. There are typically three foot pedals or buttons that control the on/off selection for the three hand drill functions.

As further contemplated for the dental drill system of the present invention, a dental station is preferably provided with a plurality of hand drills having different drilling bits as may be required by the dentist. It is impractial to have separate foot controls for each hand drill and thus the system includes additional controls for establishing which of the hand drills are being controlled by the three foot controls.

Obviously the dentist has enough to concentrate on while working on a patient without also having to concern himself with all of the various controls that have to come into play. It is therefore an object of the present invention to provide a system that allows the dentist to select one of a plurality of available hand drills, and by the selection process, automatically interconnect the foot controls to that hand drill. The selected hand drill receives full utilization of the air and water supply to the system and full control of the functions through the foot controls. The non-selected hand drills remain on standby but are disconnected from the air and water supplies until the dentist chooses to select another of the hand drills. Upon such a selection change, the water and air supplies, as well as the control mechanism, are automatically diverted to operate the newly selected hand drill.

BRIEF DESCRIPTION OF INVENTION

The foot control unit of the preferred embodiment of the invention is connected to three air lines identified as the drive and cooling air line, the chip air line, and the water control air line. The mechanism in the unit introduces air pressure into selected ones of the air lines upon activation of one of three foot controlled valves, i.e. one foot valve pressurizes the chip air line, a second foot valve pressurizes the drive and cooling air line, and a third foot valve pressurizes both the drive and cooling air line and the water control air line.

The three lines of the foot control unit plus two additional lines including a separate water line from a water source and an air line from an air pressure source (to provide air for syringe operation) are connected into the side of a manifold unit. A plurality of modules are fastened end to end, first to the manifold (on either or both sides) and then to each other. Preferably a syringe block is also attached to either end of this setup. A first network of orifices extend through the manifold and modules i.e. there are six individual orifices each extending continuously through the setup of modules and manifold. The five lines are each connected into one of the six orifices of this first network, the sixth orifice being interconnected to a pressure gauge mounted in the manifold. It will thus be understood that syringe air pressure and water are continuously available at all times within all of the modules, and chip air pressure, drive and cooling air pressure, and water control air pressure are available to all of the modules as determined by foot actuation of the foot control valves.

As concerns operation of the hand drill, four of the pressurized orifices (three air and one water) supply the three lines of the hand drill, i.e. one line with turbine drive air pressure during either a dry drilling or wet drilling operation, a second line with cooling and cleaning air pressure for air cooling, mist cooling or chip air cleaning operation, and the third line with water to be mixed with the cooling air for mist cooling. The conversion of air and water pressures from the primary orifice network to the hand drill lines is accomplished by a secondary orifice network contained within each module (but note that the secondary orifice networks are not interconnected with each other).

An interconnection between the primary and secondary orifice networks is controlled by a plurality of valves that are opened and closed by movement of valve stems. They are biased open, and are closed by a toggle switch that is provided on an arm member pivotally connected to the module. The arm member also carries a hand drill holding cradle. Placement of the hand drill into its holding cradle pivots the arm member and closes the valves of that module, while removal of the hand drill from the cradle opens the valves. Thus whichever of the hand drills is removed from its holding cradle, that module permits passage of water and air into the hand drill as determined by selective actuation of the foot control valves.

In addition to the novel system as outlined above, the valves are believed novel and beneficial for insuring the workability of the system. These valves in part rely on rubber balls that close and open various orifices activated by air pressure. The system, the valves, and the various other components that operate the system of this invention will be more clearly understood by reference to the following detailed description and drawings wherein:

FIG. 5 is a bottom plan view of the automatic selection controls setup of FIG. 1;

FIG. 6 is a view of one element of the automatic selection controls setup as taken on view lines 6—6 of FIG. 7;

FIG. 7 is a sectional view of one element of the setup as taken on view lines 7—7 of FIG. 1;

FIG. 8 is a partial view of the element of FIG. 7 illustrating a second control position of the element;

FIG. 11 is a sectional view as taken on view lines 11—11 of FIG. 1 with portions removed to illustrate another of the control functions of the setup;

FIG. 12 is a sectional view as taken on view lines 12—12 of FIG. 1 similar to FIG. 11 but illustrating a second position of the control function;

FIG. 13 is a view as taken on view lines 13—13 of FIG. 10;

THE DENTAL STATION IN GENERAL

Figure 1:
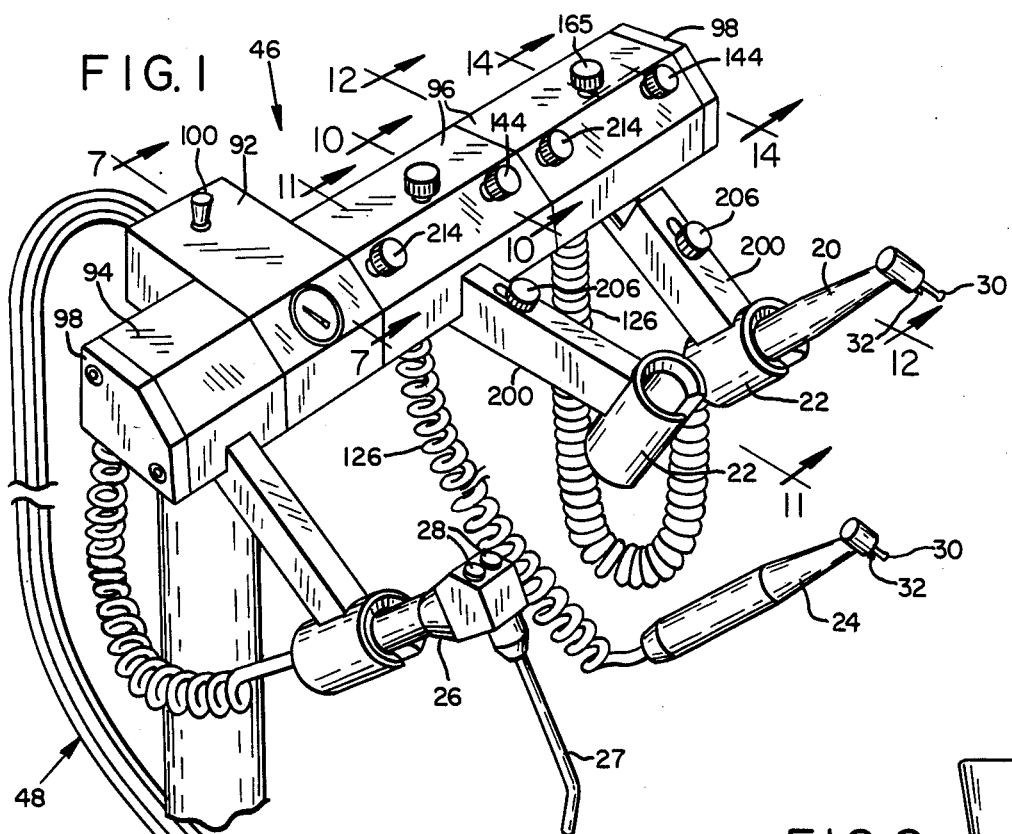
FIG. 1 is a perspective view of a dental station including hand drills, foot controls and automatic selection controls incorporating the dental system of the present invention.

Reference is made to FIG. 1 wherein the major components of the invention are illustrated in general. There are two hand drills illustrated, one drill 20 being mounted in its holder 22 and a second drill 24 being removed from its holder as when held by a dentist during work on a patient's teeth.

A dental syringe 26 is used strictly for cleaning and is capable of emitting either air or water under pressure through the syringe nozzle 27 by manipulation of on/off switches 28 on the syringe. The dental hand drills 20 and 24 are capable of three functions that include: (a) drilling with drill bits 30 coupled with cooling air emitted from nozzle 32, (b) drilling with drill bits 30 coupled with cooling mist, a mixture of air and water emitted from nozzle 32 and (c) cleaning of the work area (no drilling) with air only emitted through nozzle 32.

The three functions of the dental hand drills 22 and 24 are controlled by a foot control unit 34 having three foot control valves. Valve 36 actuates the function (a) of drilling coupled with cooling air, i.e. depressing the valve 36 opens the air lines (to be explained hereafter) for directing air to the hand drill for driving the drill bit and also for directing air to the hand drill to be emitted from nozzle 32. A second valve 38 actuates the function (b) of drilling coupled with cooling mist i.e. both the above air lines plus a third air line is opened that allows water to intermix with the cooling air in the hand drill to form a cooling mist that is emitted from the nozzle 32. The third valve 40 actuates the function (c) by opening the air line to the nozzle 32 for directing chip air onto the work area.

The various lines and controls that convert the opening and closing of the foot valves 36, 38 and 40 into the selected drilling, cooling, and cleaning operations will be explained in later sections. For the purpose of general understanding, it will suffice for the reader to understand that air from an air source (not illustrated) is connected through a line 42 into the foot control unit 34, and water from a water source is connected through line 44 into the control setup 46 where valving is actuated by a water control air line from valve 38 to allow water from line 44 to flow through nozzle 32. This same water source and a direct air source into the control setup 46 provides air and water to the syringe 26 to be directed out its nozzle 27 by actuation of control buttons 28.

For actuation of the hand drills 20, 24 (as differentiated from the syringe 26) the bundle of lines designated 48 in FIG. 1 carries three air lines from the foot control 34 to the control setup 46. The control setup 46 comprises a complex array of orifices, chambers and valving that converts the air pressure of these air lines to appropriately direct air and water into a designated one of the hand drills i.e. drill 24 which is removed from its cradle 22.

THE FOOT CONTROL UNIT

Figure 2:
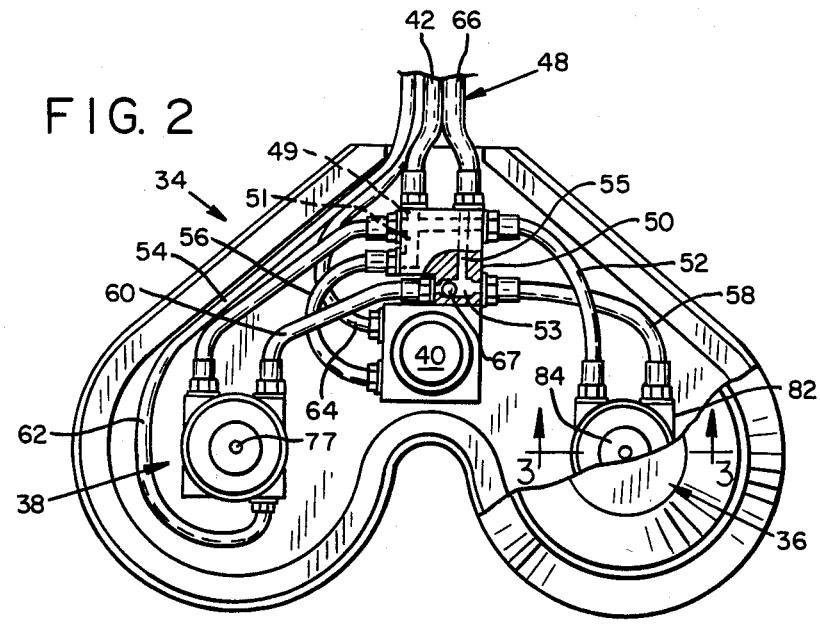
FIG. 2 is a plan view, with portions removed, illustrating the foot controls of FIG. 1.

Reference is made to FIG. 2 illustrting the foot control unit 34. Contained within the unit 34 is an air transfer block 50 containing an air inlet chamber 51 and an air outlet chamber 53. Line 42 (the line from the air source) through portal 49 provides air pressure to the inlet chamber 51 of block 50. Air line 52 interconnects this inlet air chamber 51 (and the pressure therein) with the inlet side of valve 36. Air line 54 interconnects the inlet air chamber 51 with the inlet side of valve 38, and air line 56 interconnects the inlet air chamber 51 with the inlet side of valve 40. Thus air pressure provided by line 42 is available to each of the valves 36, 38 and 40.

A return line 58 interconnects the exit side of valve 36 with the outlet air chamber 53 of block 50, and return line 60 interconnects the exit side of valve 38 with the outlet chamber 53. An outlet line 62 from valve 38 passes directly out of the foot control unit to join bundle 48 and is referred to as the water control air line 62. Similarly, an outlet line 64 from valve 40 passes directly out of the foot control unit to join bundle 48 and is referred to as the chip air line 64. An outlet air line 66 is interconnected with outlet air chamber 53 through portal 55 and thus directs air pressure from either of the return lines 58 or 60 to outlet line 66 which is referred to as drive air line 66.

In operation only one of the valves 36 or 38 will be activated to pass air pressure into outlet chamber 53. The passive return air line of the other valve (either line 58 or line 60) will be opened to exhaust air pressure from the outlet side of the valve (as will be explained with reference to FIGS. 3 and 4) and thus it is desirable to provide a positive closure of the interconnection between the passive line and the outlet air chamber 53. This is accomplished by a rubber ball 67 in the chamber 53 that is movable to one or the other of the interconnecting portals between return lines 58 and 60 and the chamber 53. Whichever of these return air lines is pressurized, the ball will be moved across the chamber to close the inlet of the passive air line.

Figure 4:
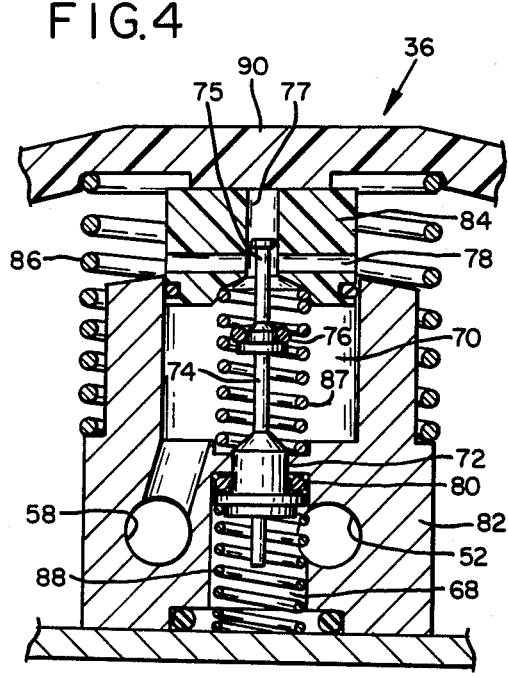
FIG. 4 is a view similar to FIG. 3 but showing the valve in a closed position.
Figure 3:
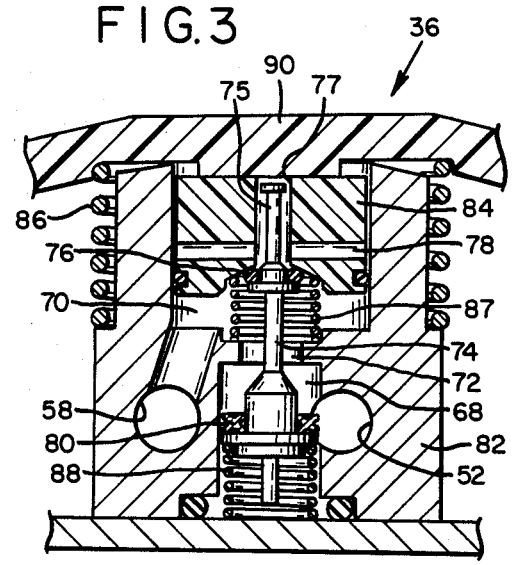
FIG. 3 is a sectional view as taken on view lines 3—3 of FIG. 2 illustrating one of the valves in an open position.

FIGS. 3 and 4 illustrate the inner structure of valve 36. Within valve 36 are inlet and outlet air chambers 68 and 70 respectively, which chambers are connected by an internal port 72. A configured valve stem 74 is movable up and down through the port 72 and within the two chambers. The top of stem 74 carries a sealing ring 76 that is adapted to seal the outlet chamber 70 from exhaust portal 78 when the valve is opened (FIG. 3), and the bottom of stem 74 carries sealing ring 80 that is adapted to seal the port 72 between the chambers when the valve is closed (FIG. 4).

As viewed in FIG. 4, valve 36 is comprised of a base member 82 and a plunger member 84 that interfits the base member 82 to define the valve interior. An external spring 86 and an internal spring 87 urges the plunger member 84 into its upper or expanded position as illustrated in FIG. 4. An internal spring 88 in chamber 68 urges the valve stem 74 to its upper position as also illustrated in FIG. 4. Thus, as shown in FIG. 4, air pressure from line 52 pressurizes chamber 68 but that pressure is prevented from entering chamber 70 by reason of sealing ring 80 closing off port 72. Chamber 70 is opened to exhaust portal 78.

When the cap 90 is stepped on by the dentist, the plunger member 84 collaspses into the base member 82, depressing springs 86 and 87. The valve stem 74 does not initially move, being stabilized by the valve stem head 75 guided in opening 77 of the plunger member 84. Sealing ring 76 then engages the mouth of opening 77 to seal off the channel between chamber 70 and exhaust portal 78. Continued downward movement of the plunger member 84 (which now carries with it the valve stem 74) unseats sealing ring 80, collapsing spring 88 and opening the port 72 between the two chambers 64 and 70. Thus air pressure passes from the inlet line 52 through chambers 68 and 70 to the return line 58.

THE CONTROL SET UP

Reference is again made to FIG. 1 wherein the control setup 96 is generally disclosed. This control setup is comprised of a manifold 92, a syringe block 4, two hand drill modules 46 and end caps 98. As will be apparent from the following explanation, any number of modules 96 can be interconnected into the control setup 46 and they can be arranged on either side of the manifold. A criteria of the disclosed setup (again as will become apparent) is that the syringe block be positioned on one end of the setup either directly to the manifold as shown or to a module on one end or the other.

First it will be generally explained that a master on/-off switch in the form of plunger 100 is provided in the manifold 92 (see FIGS. 1, 7 and 8). The plunger 100 moves a valve stem up and down within a channel 102. The valve stem carries a seal 104 that is movable with the stem to an upper position as seen in FIG. 8 or to a lower position as seen in FIG. 7. Referring now also to FIG. 6, an air inlet 106 and an air outlet 108 are connected to the chamber 102. These inlet and outlets are in communication with each other through channel 102 with seal 104 in its raised position of FIG. 8, and such communication is blocked by the seal in its lower position of FIG. 7. The air source and water source are turned on and off by air pressure from outlet 108. Thus with the master switch in the off position of FIG. 7, neither air or water will be available for any of the functions hereafter to be described. With the master switch in the closed position of FIG. 7, air in the passageway of outlet 108 is exhausted through valve channel 102 around the bottom of the valve stem.

CONTROL SETUP—PRIMARY ORIFICE NETWORK

Reference is made to FIGS. 6, 7 and 11 which illustrate the primary orifice network of the control setup. With the manifold 92 and modules 96 coupled together as shown in FIG. 1, (such coupling being achieved by aligning bolts and pins generally designated throughout by the reference number 19) a total of six orifices are aligned and continuous through the manifold and modules. First, from FIG. 7, note that the water line 44 is connected into the manifold and channeled (dash lines) into the water orifice 110 which provides water through a continuation of water orifice 110 to all of the modules (FIG. 11). Also note that an air line 112 directly from the air source is channeled into the syringe air orifice 114. Syringe block 94 has orifices 110 and 114 to provide water and air to the syringe 26. Because this syringe block may be coupled to a module rather than to the manifold as shown, this syringe air orifice 114 is provided in modules 96 although such orifice in the modules has no functions except to make the syringe air available to a syringe block that may be coupled to it. The water orifice 110 does have a function in the modules as will be explained. However, in that the remaining orifices are for module use only, and because the syringe block is only located at an end position, the remaining orifices to be now explained are common only to the manifold and modules.

The water control air line 62 is connected to the manifold 92 and channeled to water controlled air orifice 116 forming the third orifice of the primary orifice network. The drive air line 66 is connected to the manifold and channeled to the drive air orifice 118 and the chip air line 64 is connected to the manifold and channeled to the chip air orifice 120, thus forming the forth and fifth orifices of the primary orifice network. The sixth orifice 122 is a gauge air orifice that is connected to a pressure gauge 123 as illustrated in FIG. 7. The manner in which these six orifices are utilized to control a selected hand drill will be described in the following section. It is important at this point to understand that valve 100 controls all functions by turning off the air and water at the source. With valve 100 open, air and water under pressure are present in orifices 114 and 110 respectively. Air pressure to orifices 116, 118 and 120 are controlled by the opening and closing of the foot valves as previously explained. Air pressure to orifice 122 is controlled by the secondary orifice network which will now be explained.

CONTROL SETUP—SECONDARY NETWORK

Reference is first made to FIG. 5 which is a bottom plan view of the control setup 46. Four line connections are provided to each of the modules 96 for conveying water and air to the hand drills. These four line connections include a drive air line connection 124. Connection 124 transmits air pressure to the dental hand drills 22, 24 through the "line bundle" 126 shown in FIG. 1 (a composite of four lines leading from the module to the hand drills). Connection 128 is simply an exhaust line connection that exhausts the spent drive air from the hand drill back to the module (through line bundle 126) where it is directed out through filter 127 through the back of the module. Connection 130 provides chip air and cooling air from the module through a third line of line bundle 126 to the hand drill (to be emitted through nozzle 32). Connection 132 provides water from the module through a fourth line of line bundle 126 to the hand drill. Referring now to FIG. 13, shown therein is a pattern of the secondary orifice network looking at the bottom of one of the modules 96 but with the bottom plate 134 having been removed. Note that the four line connections 124, 128, 130 and 132 are superimposed onto the pattern of FIG. 13 in dash lines.

CONTROL OF WATER TO THE WATER CONNECTION 132

Figure 10:
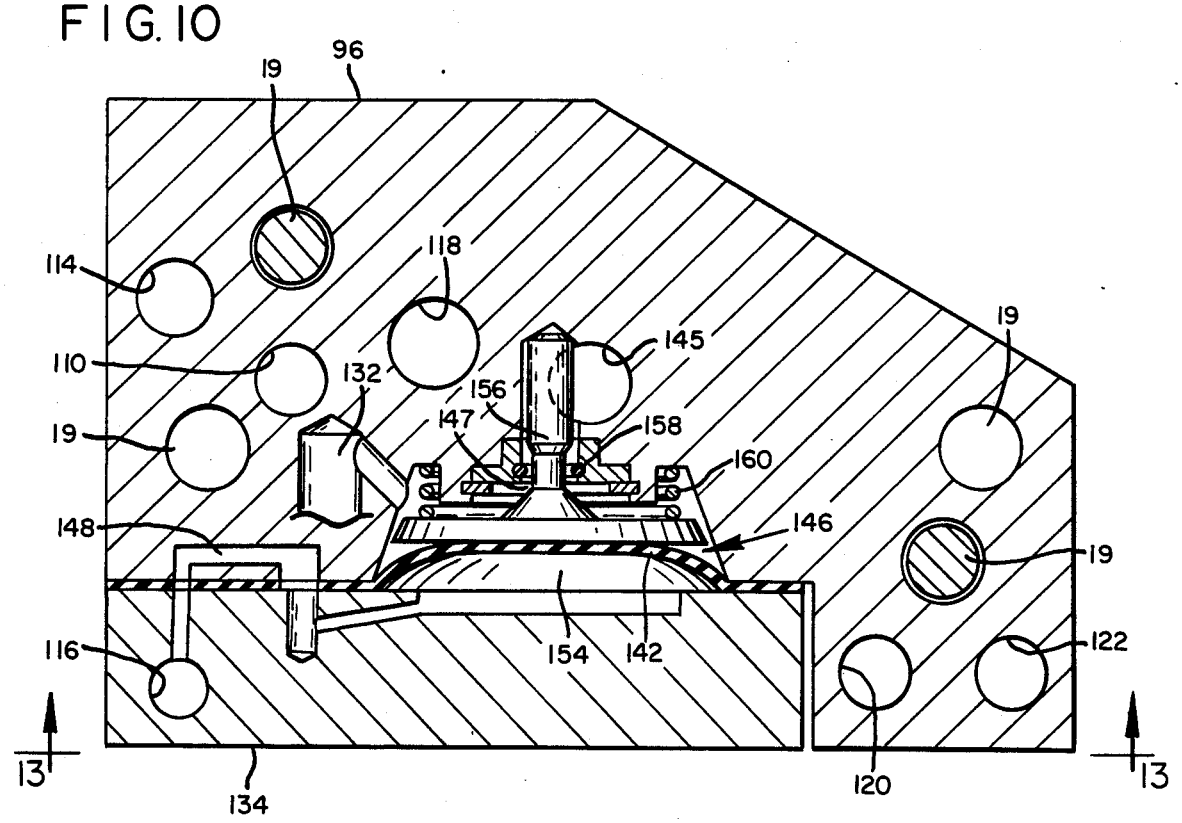
FIG. 10 is a sectional view as taken on view lines 10—10 of FIG. 1 with portions removed to illustrate one of the control functions of the setup.

As explained, water is available to the modules within the orifice 110 of the primary orifice network. Within the secondary orifice of FIG. 13, orifice 136 communicates directly with orifice 110. Channel 138 directs the water to orifice 140 which directs the water to a pressure adjustment valve 144 (FIG. 14) and then through orifice 145 to the top of the diaphragm 142 (FIG. 10). With the diaphragm control 146 opened, water is directed through orifice 147 to connection 132. Thus water from the orifice 110 must first pass through adjustment valve 144 and then the diaphragm control 146 before it is passed on to the hand drill.

Opening and closing of the diaphragm is accomplished by air pressure through orifice 116 of the primary orifice network. In FIG. 13, orifice 148, including plunger/ball valve 150, communicates with the orifice 116, and channel 152, in cooperation with a mating channel portion in plate 134 (see FIG. 10) directs air pressure into chamber 154 of the diaphragm control. Pressure in the chamber 154 raises plunger 156, unseating the plunger from seal 158 (as shown in FIG. 10) allowing water from orifice 145 to pass through the control to line connection 132. Thus as determined by the foot control valves, with line 116 pressurized, and with plunger/ball valve 150 opened (to be later explained) water from line 110 is directed to the water line connection 132 through the adjustment valve and control valves. Again as determined by the foot control valves, if line 116 is depressurized, so is chamber 154 of the diaphragm control and spring 160 forces the plunger 156 down to seal off the water flow.

CONTROL OF DRIVE AIR TO CONNECTION 124 AND COOLING AIR TO CONNECTION 130

Figure 16:
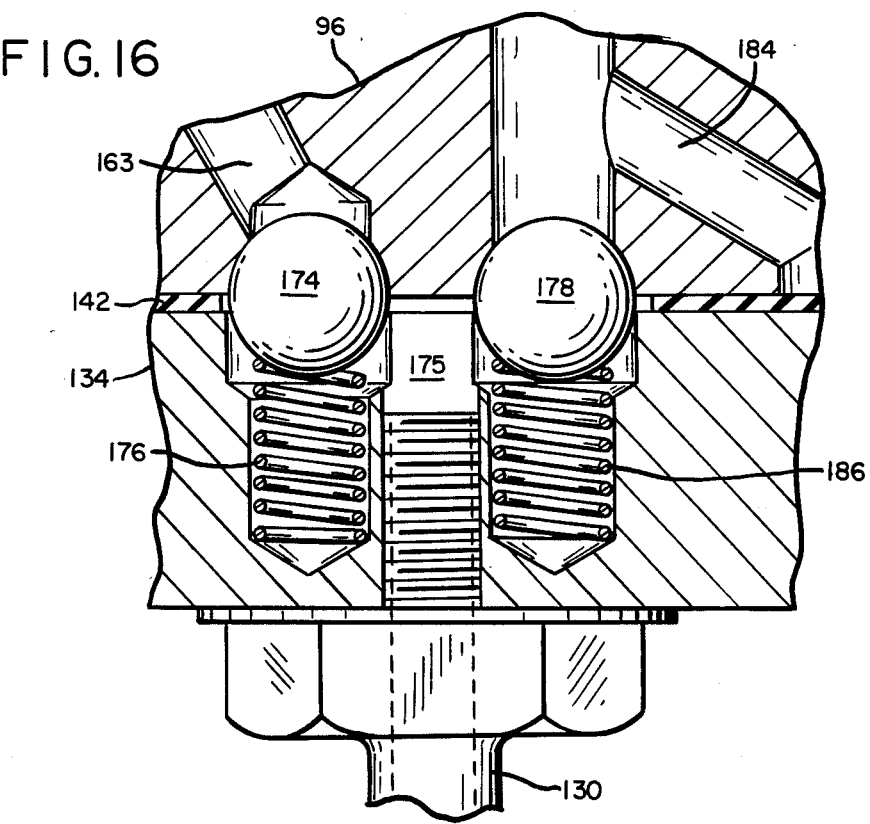
FIG. 16 is an enlarged view of one of the valve controls incorporated in the setup of FIG. 1.
Figure 14:
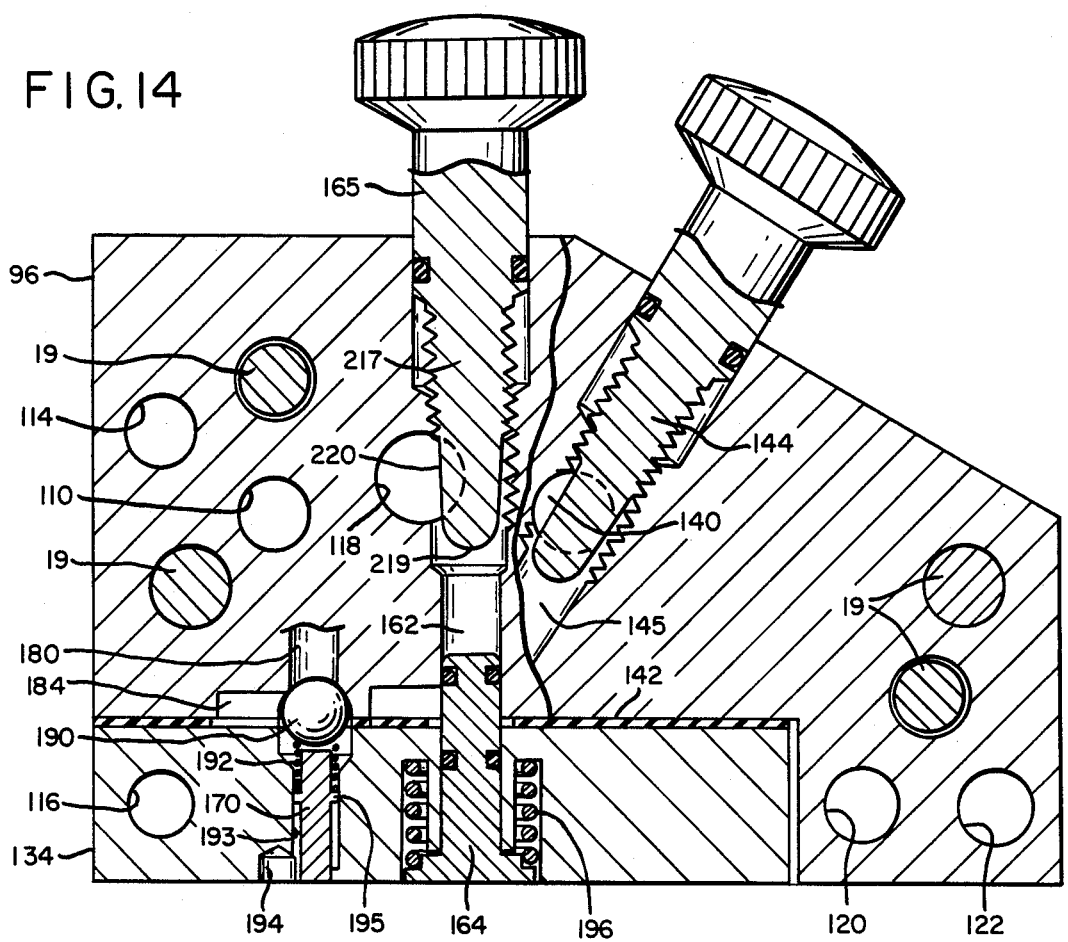
FIG. 14 is a view taken on view lines 14—14 of FIG. 1.
Figure 15:
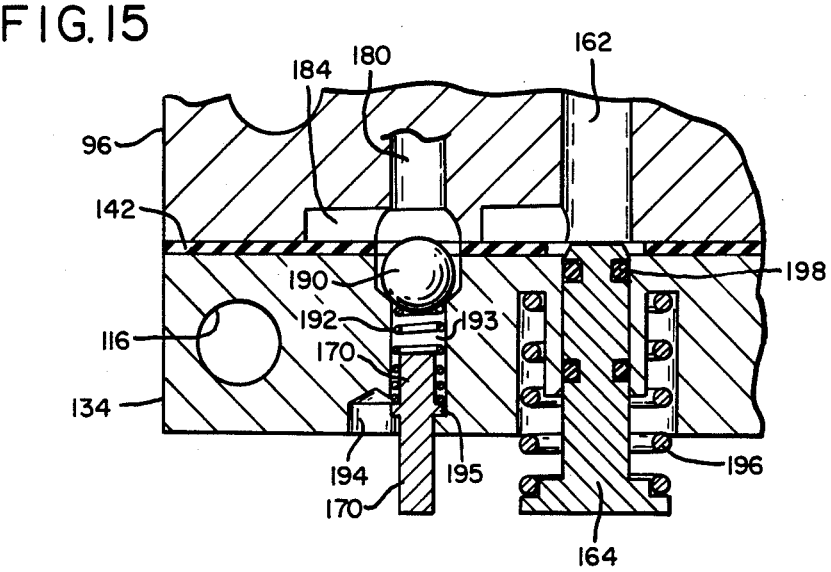
FIG. 15 is an enlarged partial view of a portion of the control unit of FIG. 14.

Again referring to FIG. 13, orifice 162 is connected to the drive air orifice 118 through a plunger valve 164 and adjustment valve 165 (see FIGS. 14 and 15). Channel 166 connects orifice 162 to orifice 168 which connects back into orifice 122 of the first orifice network (and thus to pressure gauge 123). A plunger/ball valve 170 in the orifice 168 is adapted to open and close this connection which will be later explained. A second channel 172 connects orifice 162 with orifice 163. Orifice 163 is connected to line connection 124 and also to one side of a double valve arrangement illustrated in FIG. 16. A rubber ball 174 in the double valve arrangement is urged by spring 176 to close orifice 163 (but not to connection 124). With orifice 163 pressurized, the spring 176 is depressed and air from orifice 163 passes around the ball 174 into chamber 175 and out chip and cooling air connection 130. Such pressure from orifice 163 also acts against ball 178 to tighten the closure of the other side of the double valve to avoid leakage of the air in chamber 175 out through orifice 184.

Thus it will be appreciated that with air pressure provided in drive air orifice 118 of the primary orifice network (as determined by the foot control valves) and with plunger valve 164 opened (to be explained further in a later section), air pressure passes into channel 166 through plunger/ball valve 170 and back to the pressure gauge (FIG. 7); and furthermore, air pressure passes into channel 172 through orifice 163 and into line connection 124; and still further, air pressure passes through the ball valve 174 and into cooling air line connection 130.

CONTROL OF CHIP AIR TO CONNECTION 130

Referring again to FIGS. 13 and 16, orifice 180 is connected through plunger/ball valve 182 into the chip air orifice 120. Channel 184 connects orifice 180 to the other side of the double valve arrangement which controls interconnection with chamber 175 and through line 130 through the ball valve 178. A spring 186 urges closure of the channel 184. When chip air is provided to channel 184, the spring 186 is depressed and chip air from channel 184 passes into chamber 175 and out through line connection 130. Also, as illustrated, with air pressure from 184 pressurizing chamber 175, pressure is applied to the underside of ball valve 174 to securely close channel 163 and prevent leakage of air into the non-pressurized drive and cooling air line, portal and channel complex.

MODULE SELECTION

Reference is now made to FIGS. 11, 12, 13, 14 and 15. As explained in the prior section with reference to FIG. 13, air pressure from drive air orifice 118 is closed and opened to the secondary orifice network by plunger valve 164 in orifice 162; air pressure from chip air orifice 120 is closed and opened by plunger/ball valve 182 in orifice 180; air pressure from water control air orifice 116 is controlled by plunger/ball valve 150 in orifice 148; and air pressure from the drive air channel complex back to gauge air line 122 is controlled by plunger/ball valve 170 to orifice 168. With all of these valves (164, 182, 150 and 170) closed, there will be no water or air passed from the module to its hand drill.

As will be appreciated from FIG. 13, valves 182, 150, 170, and 164 are grouped together and excessible to a toggle arm 188 shown in dash lines in FIG. 13. Referring to FIGS. 14 and 15, plunger/ball valve 170 is representative of valves 150 and 182. FIG. 15 illustrates valve 170 in an opened position with the plunger of valve 170 in its lower position within valve chamber 193 and partially protruded outside the module. FIG. 14 illustrates the closed position with the plunger forced to its upper position within valve chamber 193 which depresses spring 192 and thereby urges ball 190 against the orifice inlet to chamber 193. Whereas it can happen that air from orifice 180 can initially (prior to full seating) leak under the ball and create a balancing pressure to the underside of the ball and thus inhibit seating, this is avoided by providing a positive exhaust portal 194. The flange 195 which guides the plunger and supports return spring 192, also prevents rapid exhaust of such leaking air under the ball and thus allows the build up of the balancing pressure. With portal 194 being open to the valve chamber above flange 195, such initially leaked air is exhausted through portal 194, and such exhaustion of air assists the seating of the ball 190 in the lower position.

Plunger valve 164 is urged into an opened position by spring 196. A sealing ring 198 on the plunger valve is movable into and out of orifice 162. In the opened position of FIG. 15, a head portion of valve 164 protrudes out of the module and available for manipulation outside the module as will be explained.

Reference is now made to FIGS. 11 and 12. Toggle arm 188 is an extension of the arm 200 that carries the holding cradle 22 for the hand drill 20. The arm 200 is pivotally connected at pivot point 202 to the module just forward of the four plunger protrusions. Toggle arm 188 is designed to simultaneously engage all four plungers to effect closure of all four valves with the cradle arm pivoted downwardly as illustrated in FIG. 12 (the valve positions being illustrated in FIG. 14). Conversely, with the cradle arm pivoted to its upper position the toggle arm is pivoted away from the valves and they are thereby opened as illustrated in FIGS. 11 and 15.

The arm 200 is appropriately balanced so that the offsetting forces of the weight of toggle arm 188 and the spring 196 of valve 164 will normally retain the arm in its upper or opened position as shown in FIG. 11. However, the weight of the hand drill placed in the cradle 22 will offset that balance and the arm 200 will pivot down causing toggle arm 188 to pivot upwardly to close the valves. Thus it will be appreciated that the simple selection of one hand drill over the other, i.e. the removal of hand drill 24 in FIG. 1 from its cradle, while hand drill 20 remains positioned in its cradle, will direct the air and water flow within the primary orifice network (as determined by the foot control valves) to hand drill 24.

In certain instances, a positive closure of the four valves of a module may be desirable, e.g. with one hand drill removed from its cradle by an assistant for the purpose of changing a drill bit while another of the hand drills is being used by the dentist. In such an instance, a positive lock mechanism such as illustrated in FIGS. 11 and 12 may be utilized. An elongated pin 204 is fixed to a screw holder 206 by lock screw 207 that is slidible in slot 208. With the cradle arm 200 forced into its lower position, the pin 204 is slid back under the module as illustrated in FIG. 12 to prevent return movement of the arm. Inadvertent sliding movement of the pin 204 is resisted by frictional pressure applied from spring 210. As a further convenience, an elastomeric pad 212 is applied to the top of arm 200 to reduce noise when the arm is pivoted up against the module body.

A further convenience previously mentioned but not explained is the adjustment valves 144 (for water) valve 165 (for drive air) and valve 214 (for cooling air). Each of these valves consists of a needle valve having a tapered shaft 217 that is screwed into an orifice of the second orifice network. The inner valve section at its end 218 is rounded to produce rapid initial closing i.e. from a wide opened position to an almost closed position. Thereafter the needle shaft 220 is gradually tapered, first to a 3° taper and then to a 1° taper until full closure of the orifice is achieved. This varying taper concept provides precise adjustment of air and water flowing to the drive air line, the cooling air line and water line of the hand drill.

OPERATION

Figure 9:
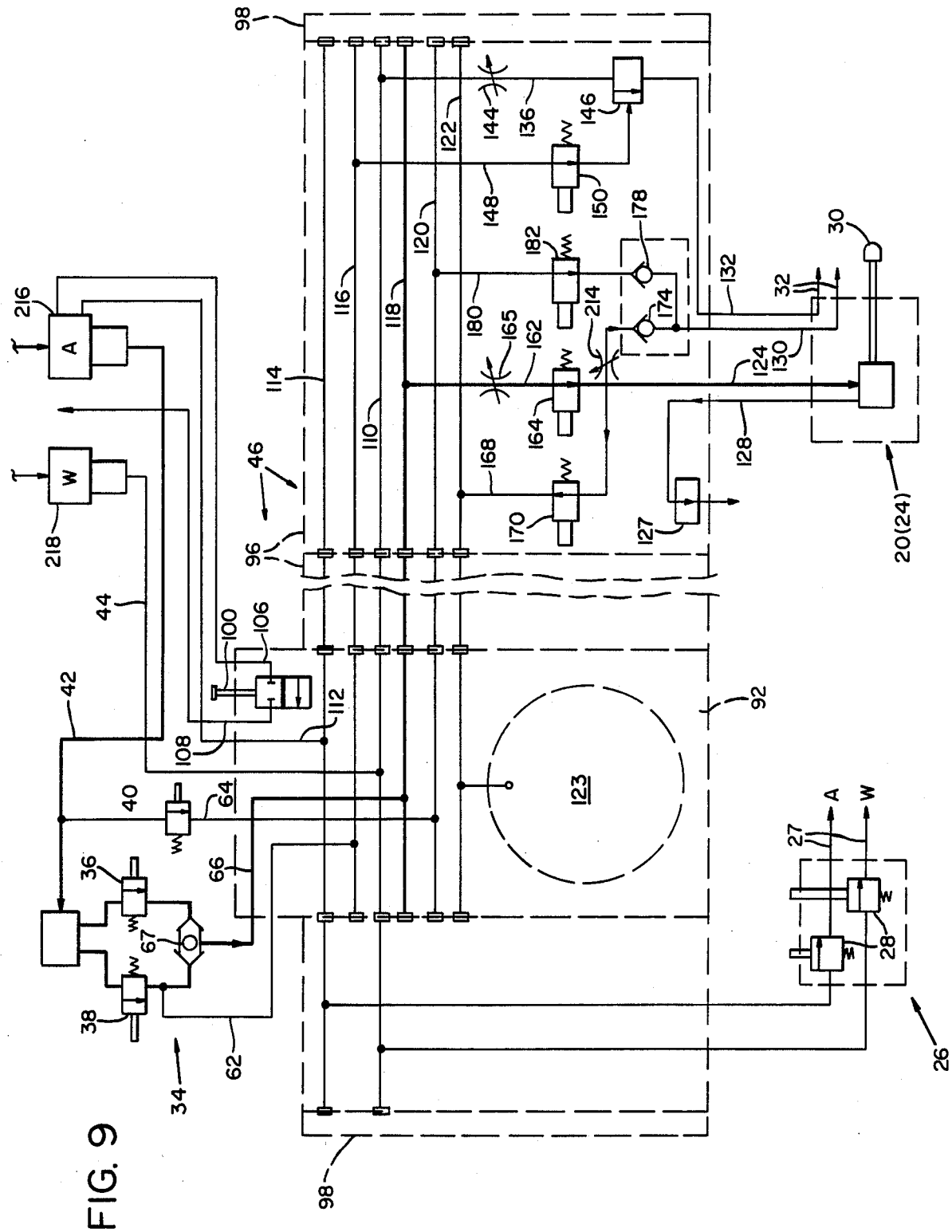
FIG. 9 is a diagramatic view illustrating the control functions of the dental system of FIG. 1.

The operation in general of the dental system is schematically illustrated in FIG. 9 and is summarized in this operation section. Water and air are supplied to the system by conventional air and water sources generally indicated at 216 and 218 respectively. The air and water sources are controlled by a master valve 100 contained in the manifold of the control setup 46. Thus air allowed through the valve 100, conveyed to and from the valve by lines 106 and 108, determines whether air is allowed into lines 42 and 112 and water in line 44.

Air pressure in line 42 pressurizes foot valves 36, 38 and 40 of foot control unit 34. Activating valve 36 sends drive and cooling air through line 66. Activating valve 38 additionally sends water control air through line 62. Actuating valve 40 sends air only through chip air line 64.

The primary orifice network contained in the control setup 46 is represented by the six orifices 110, 114, 116, 118, 120 and 122. Orifice 110 is directly connected to the water source 218 through line 44 and contains water under pressure at all times. Orifice 114 is directly connected to the air source through line 112 and contains air pressure at all times. Thus air and water to the syringe 26 is simply controlled by switches 28.

Orifice 116 is connected to the water control air line 62 and is pressurized upon actuation of valve 38. Orifice 118 is connected to the drive and cooling air line 66 and is pressurized upon actuation of either of the valves 36 and 38. Orifice 120 is connected to the chip air line 64 and is pressurized only upon actuation of valve 40.

The secondary network of each module converts the available air pressures in orifices 116, 118, 120 for controlling the pressurization of the lines to the hand drills including a drive air line 124, a water line 132 and a chip and cooling air line 130. Thus orifice 162 taps into orifice 118 and directs the air pressure (a) back to orifice 122 through orifice 168 to enable a readout of the drive air pressure at pressure gauge 123, (b) to drive air line 124 and (c) to cooling and chip air line 130 (through the double valve arrangement 174, 178). Orifice 180 taps into the chip air orifice 120 and directs air through the double valve arrangement 174, 178 to cooling and chip air line 130. Orifice 148 taps into orifice 116 and directs air pressure to the diaphragm control 146 to open water orifice 136 to water line 132.

Thus it will be appreciated that the hand drill functions to drill with cooling air, drill with mist air, or provide chip air only, depending on pressurization of orifices 116, 118 and 120. However, should the hand drill be placed in its cradle, valves 150, 164 and 182 will be closed to prevent transmission of air from orifices 116, 118 and 120 into the second network of that module. Note also that valve 170 closes off the orifice 168 to prevent back pressure when another of the hand drills provide pressure to the gauge pressure orifice 122. Also note that adjustment valves 144, 165 and 214 adjust water pressure and air pressure for the drive air and cooling functions of the hand drill.

Numerous modifications, improvements and alterations will be apparent to those skilled in the art upon a reading of the disclosure herein. However, it is to be understood that such alterations, etc. are encompassed within the concept of the invention herein as defined by the claims appended hereto.

I claim:

1. A dental drill system comprising; a foot control unit, a control setup including multiple interconnected modules, and a hand drill associated with each module, foot control lines interconnecting the foot control unit and the control setup and hand drill lines interconnecting each module and its associated hand drill, and the improvement that comprises;

said foot control unit respectively providing air pressure to three of said foot control lines for providing air for driving and cooling in one line, for chip cleaning in a second line, and for activating a water control valve in a third line, a primary orifice network in said control setup including individual orifices extended through the multiple interconnected modules, and connection means directly interconnecting the three foot control lines with three of the orifices of the primary orifice network to provide an extension of the air pressure in said foot control lines that is available through said orifices to each of the modules, and a fourth orifice connected to a water line through which water pressure is supplied independent of said foot control unit, a secondary orifice network within each module including first valve means for conveying air from the primary orifice having driving and cooling air to a first hand drill line for driving a drill bit, said first valve means further conveying air from the primary orifice having driving and cooling air and from the primary orifice having chip cleaning air to a second hand drill line, said first valve means conveying air to said second hand drill line from one of said primary orifices only while closing interconnection to the other primary orifice, a second valve means receiving water from the fourth primary orifice and air pressure from the water control orifice of said primary orifice network and in response to such air pressure conveying water to a third hand drill line, a mechanically operated valve having a valve stem projected into each of said orifice connections that is movable between open and closed positions for opening and closing the connection to the respective hand drill lines, and each of said valve stems exposed for independent manual manipulation.

2. A system as defined in claim 1 wherein said control setup includes an arm member pivoted between first and second positions, said arm member having a hand piece cradle and being urged into the first position by the weight of the hand piece contained in the cradle, and biasing means biasing the arm member to the second position with the hand piece removed from it's cradle, said exposed valve stems being grouped and positioned for engagement by the arm member in said first position to close each of the connections to the respective hand drill lines.

3. A dental drill system as defined in claim 2 wherein the valve means in said secondary orifice network includes plunger/ball valves having a valve chamber, an orifice inlet thereto, an elastomeric ball movable in said chamber to close and open said orifice inlet, said valve actuating means including a plunger, a spring having one end engaging the ball and having its other end engaging the plunger, said plunger being movable in said chamber with one end thereof protruded from the module and being engagable by the valve actuating arm portion of said arm member for depressing the spring and urging the ball to its orifice inlet closing position.

4. A dental drill system as defined in claim 3 wherein said ball is movable between closed and opened ball seating positions in said chamber, and an exhaust portal is provided to said valve chamber behind said open ball seating position to prevent pressure buildup behind the ball that may inhibit such ball seating.

5. A dental drill system comprising multiple hand drills, each having an air driven drill bit and a cooling and cleaning nozzle, a bundle of lines to each said hand drill including a drive air line, a cooling and chip air line, and water line for generating the three hand drill functions of drilling with cooling air from the nozzle, drilling with cooling mist from the nozzle, and chip air only from the nozzle; a foot control unit having three foot controls for generating the three hand drill functions, an air source providing air pressure to said foot control unit, and a bundle of lines from said foot control unit including a first line that is pressurized by the first and second foot controls for transmitting drive and cooling air, a second line that is pressurized by the second foot control for transmitting water control air, and a third line that is pressurized by the third foot control for transmitting chip air; and the improvement comprising a control setup for converting the air pressure of the foot control air lines for transmission of air and water pressure to the appropriate lines of a selected one of the multiple hand drills, said control setup including;

multiple modules corresponding in number to the multiple hand drills, said modules interconnected in sequence one to the other, and each module having a bundle of lines of one of the hand drills connected thereto, a primary orifice network in said control setup including multiple orifices independent of each other and each extending continuously through the multiple of modules, the first line of said foot control unit connected into a first orifice of said primary orifice network and providing common drive and cooling air pressure to the multiple modules, the second line of said foot control unit connected into a second orifice of said primary orifice network and providing common water control air pressure to the multiple modules, the third line of said foot control unit connected into a third orifice of said primary orifice network and providing common chip air pressure to the multiple modules, and a water source connected into a forth orifice of said primary orifice network providing common water pressure to the multiple modules;

a secondary orifice network in said control setup within each module independently connected to the primary orifice network, said secondary orifice network including an air pressure controlled water valve and a water orofice connected through said water valve to the water orifice of the first orifice network and to the water line of a hand drill, a water control air orifice in said second network connected to the water control air orifice of the first network and to the air pressure controlled water valve to open said water valve when pressurized by said water control air orifice, a drive air orifice in said second orifice network connected to the drive and cooling air orifice of said first network and to the drive air line of said hand drill to interconnect said drive air line to the drive and cooling air orifice of the primary network, a chip air orifice in said second network connected to the chip air orifice in said primary orifice network and to the cooling and chip air line of said hand drill to interconnect said cooling and chip air line to said chip air orifice of said primary orifice network, and a double valve arrangement connected between the drive air orifice and the chip air orifice of the secondary network, said double valve arrangement being responsive to air pressure in the drive air orifice to close the connection between the chip air orifice of the secondary network and chip air orifice of the primary network and open the connection between the drive air orifice and secondary chip air orifice to thereby pressurize the cooling and chip air line, and said double valve arrangement being responsive to air pressure from the chip air orifice of the primary network to open the connections thereto while closing the connection to the drive air orifice.

6. A dental drill system as defined in claim 5 wherein the control setup includes an arm member pivotally connected to each module, a hand drill holder carried by the arm member at one end thereof and an extension of the arm member beyond the pivotal connection opposite the holder that forms a toggle switch control portion, a toggle switch control valve in each of the three secondary chip air orifice, drive air orifice and water controlled air orifice, said three toggle switch control valves protruding from the module to be depressed by the toggle switch control portion for controlling the valves when the arm member is in a first pivotal position, and biasing means biasing the arm to a second pivotal position with the toggle switch portion retracted from the toggle switch control valves for opening the valves, and said arm member biased by the biasing means to its second position with the hand drill removed from the holder and being pivoted to its first position with a hand drill placed in the holder.

7. A dental drill system as defined in claim 6 wherein the toggle switch controlled valves of said chip air orifice and water control orifice are plunger/ball valves including a valve chamber having an orifice inlet thereto, an elastomeric ball movable in said chamber to close and open said orifice inlet, a plunger, a spring having one end engaging the ball and having its other end engaging the plunger, said plunger being movable in said chamber with one end thereof protruded from the module and being engagable by the toggle portion of said arm member for depressing the spring and urging the ball to its orifice inlet closing position.

8. A dental drill system as defined in claim 7 wherein said ball is movable between closed and opened ball seating positions in said chamber, and an exhaust portal provided to said valve chamber behind said opened ball seating position to prevent pressure buildup behind the ball that may inhibit such ball seating.

9. A dental drill system as defined in claim 6 including a locking means between said arm and said module to releasably lock the arm in the first pivotal position.

10. A dental drill system as defined in claim 5 wherein said double valve arrangement includes a common valve chamber, an air inlet from said drive air orifice of the second orifice network and an air inlet from said chip air orifice of the second orifice network, and an outlet from said common chamber to the cooling and chip air line of the hand drill, an elastomer ball at each air inlet movable between positions for closing and opening said air inlets to said common chamber, said open position of each of said balls determined by pressurization of the orifice leading into that inlet, and said closed position determined by depressurization of the orifice leading to that inlet while the chamber is pressurized through the other of said orifice inlets.

11. A dental drill system as defined in claim 5 wherein said control setup includes a manifold interconnected to the modules, said primary orifice network extended through said manifold, said connections of said lines from the foot control unit and water source to said primary orifice network provided in said manifold, a fifth orifice in said primary orifice network providing gauge air pressure extending through said modules and manifold, and an air pressure gauge in said manifold interconnected to said fifth orifice, and said drive air orifice of said secondary orifice network interconnected to said fifth orifice for air pressure indication of drive air pressure readable by said pressure gauge.

12. A dental drill system as defined in claim 11 including a forth toggle switch controlled valve located in the secondary orifice network at the interconnection between the drive air orifice and the fifth orifice of said primary orifice network.

13. A dental drill system as defined in claim 12 wherein said control setup includes a syringe and syringe block interconnected to one end of the interconnected modules and manifold, a sixth orifice in said primary orifice network, an air source connected into said sixth orifice, and said forth orifice and said sixth orifice extending through said syringe block to provide water and air from said water and air sources to the syringe.

14. A dental drill system as defined in claim 5 including three adjustment valves, one in the interconnection of the drive air orifice with the drive air line of the hand drill, the second in the interconnection of the drive air orifice with the cooling and chip air line of the hand drill, and the third in the interconnection of the water orifice with the water line of the hand drill, said adjustment valves including needle valve stems protruded from the modules to permit manual adjustment of the water and air passing through the valves.

15. A dental drill system as defined in claim 14 wherein the needle valve stems include multiple tapered stem sections for initial rapid adjustment of water and air pressure and subsequent fine adjustment of water and air pressure passing through said adjustable valves.

16. A dental drill system as defined in claim 5 wherein said foot control unit includes a transfer block having inlet and outlet air chambers, said inlet air chamber having an air inlet from said air source and air outlets therefrom to each of said three foot control valves, and said outlet air chamber having inlets from said first and second foot control valves, and an elastomeric ball in said outlet chamber movable between the inlets thereto to close off the inlet of the passive valve in response to air pressure from the activated valve.

* * * * *